United States Patent [19]

Lehnhoff et al.

[11] 4,243,530
[45] Jan. 6, 1981

[54] HAEMOFILTRATION WITH FILTRATE FLOW CONTROL BY ADJUSTABLE VENTING

[75] Inventors: Kurt Lehnhoff, Oberursel; Wilfried Schael, Bad Homburg, both of Fed. Rep. of Germany

[73] Assignee: Dr. Eduard Fresenius Chemisch-pharmazeutische Industrie KG, Apparatebau KG, Bad Homburg, Fed. Rep. of Germany

[21] Appl. No.: 966,495

[22] Filed: Dec. 4, 1978

[30] Foreign Application Priority Data

Dec. 9, 1977 [DE] Fed. Rep. of Germany ....... 2754810

[51] Int. Cl.³ .............................................. B01D 31/00
[52] U.S. Cl. .................... 210/137; 210/472; 210/321.3; 210/416.2
[58] Field of Search ......................... 128/274, DIG. 3; 137/510; 210/321 A, 321 B, 137, 416, 90, 120, 130, 133, 472

[56] References Cited

U.S. PATENT DOCUMENTS

| | | | |
|---|---|---|---|
| 3,140,726 | 7/1964 | Arenhold | 137/510 |
| 3,212,642 | 10/1965 | Kylstra | 210/321 B |
| 3,242,942 | 3/1966 | Gould | 137/510 |
| 3,520,298 | 7/1970 | Lange | 128/213 |
| 3,626,670 | 12/1971 | Pecker | 210/321 B |
| 3,939,069 | 2/1976 | Granger et al. | 210/22 A |
| 3,946,731 | 3/1976 | Lichtenstein | 128/214 R |
| 4,060,485 | 11/1977 | Eaton | 210/87 |

OTHER PUBLICATIONS

Hamilton, R. et al., "Blood Cleansing By Diafiltration in Uremic Dog and Man", A.S.A.I.O. vol. 17, 1971, pp. 259-265.
Perry, R. H. et al., Chemical Engineers Handbook, 5th Edition, McGraw Hill Book Co., 1973, pp. 22-88 to 22-91.
Henderson, L. et al., "Uremic Blood Cleaning by Diafiltration . . .", A.S.A.I.O., vol. 16, 1970, pp. 107-114.

Primary Examiner—Charles N. Hart
Assistant Examiner—David R. Sadowski
Attorney, Agent, or Firm—W. G. Fasse; D. F. Gould

[57] ABSTRACT

A haemofiltration apparatus includes a combined blood pump (1a) and filtrate pump (1b). The pressure on the inlet side of the filtrate pump may be adjusted by a cone valve (14) mounted on a diaphragm (12) which opens to admit air when the inlet pressure falls below a predetermined value which is set by a valve spring (16) provided with an adjustment screw (15). The other side of the diaphragm may be connected to the atmosphere or to an air trap (6) in the blood pump circuit.

9 Claims, 1 Drawing Figure

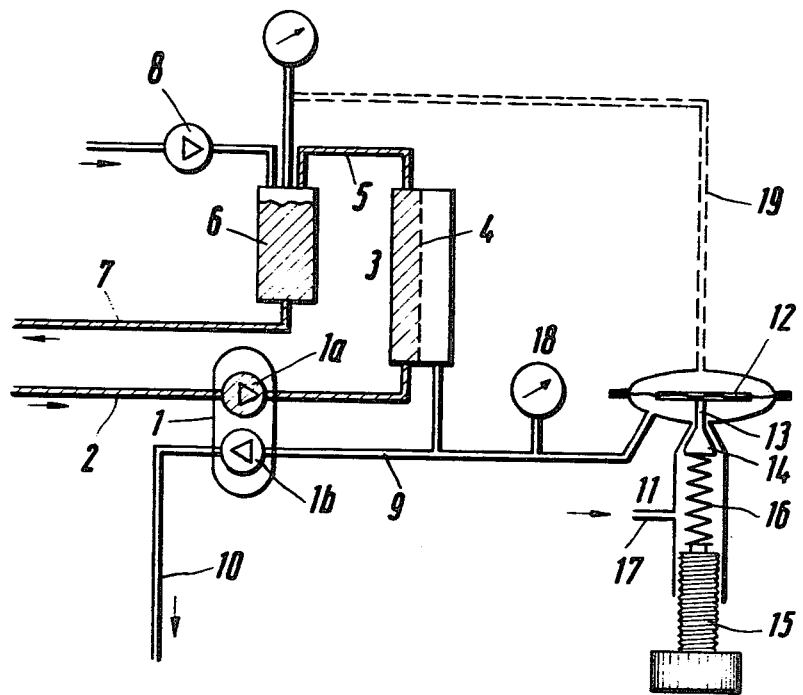

HAEMOFILTRATION WITH FILTRATE FLOW CONTROL BY ADJUSTABLE VENTING

BACKGROUND OF THE INVENTION

The invention relates to apparatus for carrying out so-called haemofiltration or haemodiafiltration. In this process of medical treatment, which provides a substitute for the natural kidney function, the blood of the patient is passed along the surface of a filter membrane in an extracorporal blood circulation, and subsequently returned to the patient. A filtrate is produced by a negative pressure on the other side of the membrane, the filtrate inter alia including the urine-bearing substances which are normally to be excreted by way of the kidneys. At the same time, a substitute fluid is mixed with the blood, in accordance with the amount of filtrate produced, in order to maintain a balance in the respective volumes of fluid involved.

In order to produce a sufficient pressure differential between the two sides of the membrane, it is usual to operate with a reduced pressure on the filtrate side. For example, it is known from the literature (L. W. Henderson et al: Kinetics of Haemofiltration, Journal of Laboratory and Clinical Medicine 85 (1975), 372–391), to use an adjustable vacuum source which is not specified in greater detail and which sucks air out of a vessel into which the filtrate flows. In other known equipment for haemofiltration, tube pumps are used to produce the reduced pressure, the tube pumps sucking off the filtrate and conveying it away into a collecting vessel. The pump speed is automatically set by way of an electronic controller in such a way that either a given increase in volume per unit of time occurs in the collecting vessel, or a given preselected pressure is maintained at the input of the pump. In the latter process which is generally considered as being more advantageous, because it can be more easily used for different types of filters, without consideration of the transmissiveness thereof, it is possible to use either a continuous pressure control or a two-point pressure control. Both cases require measuring means for the pump input pressure, which have an electrical output either in the form of a switching means for switching the pump on and off (two-point control) or in the form of an analog signal generator for continuously controlling the pressure by way of an electronic controller which is connected upstream of the pump motor.

In the known apparatus, the total expenditure is considerable, comprising at least the pump, a pressure measuring means with an electrical output and the controller for the pump drive.

OBJECT OF THE INVENTION

It is the object of the present invention to provide a simplified and thus cheaper and in particular more reliable haemofiltration apparatus. This is achieved by a particularly simple arrangement for producing the filtration reduced pressure, having the features recited in the claims.

SUMMARY OF THE INVENTION

The invention makes use of the fact that a blood pump which is in the form of a tube or hose pump is used in every case for carrying out the haemofiltration process, such blood pumps also permitting the fitting of two pump tubes, depending on the particular type. A second pump tube which is fitted into the pump head can thus be used in principle for pumping a second medium, in the present case the filtrate. It will be appreciated that this cannot be directly used for the problem set, for the optimum delivery rates for blood and filtrate are not in a fixed relationship with each other but vary independently of each other within certain limits, depending on the particular circumstances. The rate of blood flow to be set depends inter alia on the abundance of the vessel connections of the patient and typically is in the range of from 150 to 350 ml/min. The flow of filtrate which is achieved under the usual pressure conditions in the available filters is from 60 to 120 ml/min.

The problem therefore arises of adapting the delivery rate of the filtrate pump which is produced by fitting a second tube, independently of the speed of rotation which is set according to the required flow of blood, in such a way as to achieve a given reduced filtration pressure. According to the invention, this problem is solved in that a valve is connected to a branch tapping on the suction side of the filtrate pump, which valve lets in a greater or smaller amount of atmospheric air and accordingly reduces the effective delivery rate of the filtrate pump to a greater or lesser extent. In the simplest case, the valve can be an adjustable needle valve. A more constant reduced pressure value can be achieved with a self-regulating pressure holding valve.

BRIEF FIGURE DESCRIPTION

An embodiment of the invention is described hereinafter by way of example, with reference to the accompanying drawing which shows a diagrammatic view of the blood and filtrate circuit of a haemofiltration apparatus with the essential operational components.

DETAILED DESCRIPTION OF A PREFERRED EXAMPLE EMBODIMENT AND OF THE BEST MODE OF THE INVENTION

A double tube pump 1 is provided for simultaneously conveying blood and filtrate. The upper part 1a of the pump conveys the blood of the patient which flows to the pump through the tube 2, to the filter 3 where it flows along the surface of the filter membrane 4 and then passes through the line 5 into the air trap 6. The purpose of the air trap is to separate out and protect the patient from any air which has penetrated into the system. From the air trap, the blood flows through the tube 7 back to the patient. In order to replace the lost volume which occurs by the removal of the filtrate, a sterile substitute solution is added to the blood, for example by means of the tube pump 8, which conveys the substitute solution into the air trap 6 where it mixes with the blood.

In order to produce a reduced pressure and to convey the filtrate away, the lower part 1b of the double tube pump 1 is connected to the filtrate side of the filter 3 by way of the tube 9. The filtrate which is carried away from the filter passes through the tube 10 for example into a collecting container not shown. In the embodiment illustrated, an adjustable pressure holding valve 11 is provided to keep a preselected pressure on the filtrate side at a constant value. In its housing, the pressure holding valve 11 includes a diaphragm 12 which is stiffened in its central portion by means of a plate and which actuates the tapered valve member 14 by way of a pin 13. In the rest condition the tapered valve member is pressed against its seat in the housing by the setting screw member 15 by way of the spring 16, so as to prevent air from passing into the chamber on the underside of the diaphragm, by way of the inlet pipe connection 17. It is only when the reduced pressure which is produced by the suction action of the pump 1b has reached a given value that the force thereby exerted on the diaphragm 12 can overcome the force of the spring 16. This causes the tapered valve member 14 to be lifted away from its seat and air is drawn in through the inlet pipe connection 17. This opposes any further rise in the value of the reduced pressure and thus results in stabilisation of a given pressure value. This pressure value can be adjusted by means of the setting screw member 15, by observing the pressure gauge 18.

The chamber above the diaphragm 12 may be in direct communication with the atmosphere or, in a further embodiment of the invention, may be connected to the air trap 6 by way of a line 19. As a result of this arrangement, it is no longer only the filtrate reduced pressure which acts on the diaphragm 12, but the difference between that pressure and the pressure which exists in the air trap 6. If the pressure drops caused by flow phenomena are ignored, the abovementioned difference is identical to the transmembrane pressure, that is to say, the pressure differential between the blood side and the filtrate side of the filter membrane 4. As this transmembrane pressure represents the parameter which is really important for filtration efficiency, as well as for mechanical loading on the filter membrane, this arrangement is to be considered as particularly advantageous.

The above-described type of pressure holding valve only represents an example of a possible design. Other pressure-controlled valves can also be used for this purpose. In the simplest case, as mentioned hereinbefore, the invention also provides a needle valve which can replace the self-controlling pressure-holding valve, for setting the reduced pressure.

Although the invention has been described with reference to specific example embodiments, it will be appreciated, that it is intended to cover all modifications and equivalents within the scope of the appended claims.

What is claimed is:

1. A hemofiltration apparatus comprising filter housing means including blood chamber means and filtrate chamber means, filter means separating said blood chamber means from said filtrate chamber means, inlet and outlet means operatively connected to said blood chamber means, first blood hose pump means (1a) including a pump head operatively connected to said blood chamber means for establishing a blood circulatory flow through said blood chamber means, second filtrate hose pump means (1b) operatively arranged to be driven by said pump head together with said first blood hose pump means, said second filtrate hose pump means (1b) having a suction side directly operatively connected to said filtrate chamber means, bias adjustable valve means (11) operatively connected to said suction side of said second filtrate hose pump means (1b), and to an air supply, for controllably connecting said suction side of said second filtrate hose pump means with said air supply, whereby said second filtrate hose pump means may entrain through said bias adjustable valve means a quantity of air which is determined by the bias adjustment of said bias adjustable valve means to reduce the filtrate conveying capacity of said second filtrate hose pump means thereby simultaneously determining the reduced pressure in said filtrate chamber means so that the adjustment of said bias adjustable valve means determines the volume of conveyed filtrate and hence the pressure differential across said filter means.

2. The apparatus of claim 1, wherein said adjustable valve means comprise valve housing means, diaphragm means operatively held in said valve housing means, conical valve seat means, conical valve closure means operatively connected to said diaphragm means and arranged for closing said conical valve seat means, adjustable spring bias means operatively connected to said conical valve closure means, said air supply connecting means comprising air inlet means connected to said valve housing means.

3. The apparatus of claim 2, wherein said valve housing means comprise a valve chamber separated from said valve seat means by said diaphragm means, and means (19) connecting said valve chamber to the atmosphere.

4. The apparatus of claim 2, further comprising air trap means operatively connected to said blood chamber means, said valve housing means comprising a valve chamber separated from said valve seat means by said diaphragm means, and means operatively connecting said valve chamber to said air trap means.

5. The apparatus of claim 2, wherein said adjustable spring bias means comprise a valve spring and a set screw operatively arranged in said valve housing means, whereby the biasing force of said valve spring is adjustable by said set screw.

6. A hemofiltration apparatus comprising filter housing means including blood chamber means and filtrate chamber means, filter means separating said blood chamber means from said filtrate chamber means, inlet and outlet means operatively connected to said blood chamber means, first hose pump means, including a pump head operatively connected to said blood chamber means for establishing a blood circulatory flow through said blood chamber means, second hose pump means operatively arranged to be driven by said pump head together with said first hose pump means, said second hose pump means having a suction side operatively connected to said filtrate chamber, adjustable valve means operatively connected to said suction side of said second hose pump means and to an air supply means for controllably connecting said suction side to said air supply means whereby said second pump means may entrain a controllable quantity of air to reduce its conveying capacity for determining the reduced pressure in said filtrate chamber means, said adjustable valve means comprising valve housing means, diaphragm means operatively held in said valve housing means for defining a valve chamber, valve seat means, valve closure means operatively connected to said diaphragm means and arranged on the opposite side of said diaphragm relative to said valve chamber for closing said valve means upon said valve seat means, adjustable spring bias means operatively connected to said valve closure means, said air supply connecting means comprising air inlet means connected to said valve housing means, said apparatus further comprising air trap means operatively connected to said blood chamber means, and means operatively connecting said valve chamber to said air trap means.

7. The apparatus of claim 6, wherein said valve chamber in said valve housing is separated from said valve seat means by said diaphragm means.

8. The apparatus of claim 6, wherein said air trap means are operatively connected between said blood chamber means and said first hose pump means.

9. The apparatus of claim 6, wherein said adjustable spring bias means comprise a valve spring and a set screw operatively arranged in said valve housing means, whereby the biasing force of said valve spring is adjustable by said set screw for determining the pressure differential across said filter means between said blood chamber means and said filtrate chamber means.

* * * * *